United States Patent [19]
Sibi et al.

[11] Patent Number: 5,939,572
[45] Date of Patent: Aug. 17, 1999

[54] METHOD FOR PREPARATION OF CARBOXYLIC ACIDS

[75] Inventors: Mukund P. Sibi; Philip Boudjouk; Jianguo Ji, all of Fargo, N. Dak.

[73] Assignee: North Dakota State University Research Foundation, Fargo, N. Dak.

[21] Appl. No.: 09/001,166

[22] Filed: Dec. 30, 1997

Related U.S. Application Data

[63] Continuation of application No. 08/746,964, Dec. 27, 1996, abandoned, which is a continuation of application No. 08/465,400, Jun. 5, 1995, Pat. No. 5,596,111.

[51] Int. Cl.⁶ .................................................... C07C 51/16
[52] U.S. Cl. .......................... 554/138; 554/132; 554/134
[58] Field of Search ..................................... 554/132, 134, 554/138

[56] References Cited

U.S. PATENT DOCUMENTS

| | | | |
|---|---|---|---|
| 2,744,928 | 5/1956 | Smith et al. | 260/530 |
| 3,855,257 | 12/1974 | Pultinas, Jr. | |
| 3,895,040 | 7/1975 | Miyazaki et al. | |
| 4,532,079 | 7/1985 | Venturello et al. | |

FOREIGN PATENT DOCUMENTS

| | | |
|---|---|---|
| 0 122 804 | 10/1984 | European Pat. Off. |
| 0 123 495 | 10/1984 | European Pat. Off. |
| 57-4940 | 1/1982 | Japan . |
| 63-93746 | 4/1988 | Japan . |
| 1 324 763 | 7/1973 | United Kingdom . |
| WO 93/12064 | 6/1993 | WIPO . |
| WO 94/10122 | 5/1994 | WIPO . |

OTHER PUBLICATIONS

Venturello, C. et al., "Oxidative Cleavage of 1,2–Diols to Carboxylic Acids by Hydrogen Peroxide," *J. Org. Chem.*, 51(9):1599–1602 (1968).

*Primary Examiner*—Gary Geist
*Assistant Examiner*—Deborah D Carr
*Attorney, Agent, or Firm*—Merchant, Gould, Smith, Edell, Welter & Schmidt, P.A.

[57] ABSTRACT

A method for preparing a carboxylic acid is provided. The method includes contacting an olefinic compound or a vicinal dihydroxy compound with oxygen in the presence of a protic organic solvent, an inorganic oxide catalyst and a peroxidant such as hydrogen peroxide or an peralkanoic acid. The inorganic oxide catalyst includes an oxide of tungsten, molybdenum, niobium, vanadium, tantalum, titanium, or yttrium.

16 Claims, No Drawings

METHOD FOR PREPARATION OF CARBOXYLIC ACIDS

This is a Continuation of application Ser. No. 08/746,964, filed Dec. 27, 1996, now abandoned, which is a continuation of Ser. No. 08/465,400, filed Jun. 5, 1995 now U.S. Pat. No. 5,596,111, which application(s) are incorporated herein by reference.

BACKGROUND OF THE INVENTION

Carboxylic acids may be prepared using a variety of processes. Among the various procedures known, the oxidative cleavage of olefinic hydrocarbons represents a particularly attractive method due to the widespread availability of these types of raw materials. Olefinic hydrocarbons may be oxidized to carboxylic acids using a variety of oxidizing agents, including $KMnO_4$, $K_2Cr_2O_7$ and $RuO_4$. These processes are however of little practical interest because of the high cost and toxicity of the oxidizing agents (in particular with regard to $RuO_4$). There are also serious problems involved with the disposal or recovery of these oxidizing agents and/or the side products generated in the course of such reactions.

The oxidative cleavage of an olefin or a vicinal dihydroxy compound using hydrogen peroxide as the primary oxidant has also been described. The hydrogen peroxide cleavage reaction is reported to be catalyzed by tungstic acid, molybdic acid or related heteropoly inorganic acids. While this procedure represents an improvement over the other oxidative methods discussed above employing costly or toxic reagents, the use of hydrogen peroxide as the primary oxidant still has certain drawbacks. The stoichiometry of the reaction is such that at least 3 or 4 equivalents of hydrogen peroxide are required to accomplish the oxidative cleavage of a diol or olefin respectively (see equations A and B below). More typically, such cleavage reactions are run using a stoichiometric excess of hydrogen peroxide (e.g., 5–6 equivalents of $H_2O_2$).

(A) $RCHOH\text{—}CHOHR' + 2\ H_2O_2 \rightarrow RCO_2H + R'CO_2H + 2\ H_2O$ (B) $RCH\text{=}CHR' + 3\ H_2O_2 \rightarrow RCO_2H + R'CO_2H + 2\ H_2O$ While hydrogen peroxide is relatively inexpensive and does not present serious waste disposal problems, hydrogen peroxide is quite reactive and presents safety issues with regard to its handling. Moreover, hydrogen peroxide is sold as an aqueous solution and thus requires the shipping of a considerable amount of water along with the reagent. From both economic and safety standpoints, it would be advantageous if an oxygen containing gas stream, such as air, could be utilized as the major oxidant to effect the oxidative cleavage of olefins and vicinal diols.

The oxidation of vicinal dihydroxy compounds (vicinal glycols) with oxygen in the presence of a catalyst mixture which includes a cobalt (II) compound and a peroxidized tungsten or molybdenum oxide has been reported. This reaction, however, must be run in a polar, aprotic solvent such as dimethylformamide ("DMF"). Since the oxidation of an olefin to a vicinal glycol is typically run in a protic solvent such as t-butanol, this method does not allow direct oxidative cleavage of an olefin to a carboxylic acid without changing the solvent and/or other reaction conditions. In addition, the presence of a polar, aprotic solvent can make the isolation of the desired product more difficult.

SUMMARY OF THE INVENTION

The present invention provides a method for preparing a carboxylic acid through the catalytic oxidation of an olefin or a vicinal dihydroxy compound in the presence of oxygen. The method provides a short and high yielding synthesis of carboxylic acids from readily available starting materials. The method uses inexpensive, commonly available reagents and is amenable to large scale synthesis. The reaction, which is carried out under mild conditions, is characterized by short reaction times and may be run in conventional apparatus. Moreover, the present method permits the ready recovery of the catalyst and/or solvent.

The method includes contacting the olefinic compound or vicinal dihydroxy compound with oxygen in the presence of a protic organic solvent, an inorganic oxide catalyst and a peroxidant such as hydrogen peroxide or a peralkanoic acid. The peroxidant is employed in a substoichiometric amount with respect to what would be required to completely carry out the oxidative cleavage of the substrate (olefin or vicinal dihydroxy compound) to a carboxylic acid. The stoichiometric amounts required using hydrogen peroxide are shown in equations (A) and (B) supra.

A further distinction of the present method is that it uses oxygen gas as the major oxidant. The use of oxygen has a number of advantages. Oxygen is less expensive and easier to handle than hydrogen peroxide. Moreover, the use of oxygen gas as the major oxidant allows the rate of the reaction to be increased without raising the reaction temperature by employing higher pressures to increase the concentration of dissolved oxygen. Because smaller amounts of a strong oxidizing agent such as hydrogen peroxide (a "peroxidant") are required, the reaction may be carried out with less hazard to technical personnel. The use of smaller quantities of a strong oxidant also results in lower rates of corrosion of process equipment.

In addition, the isolation of the final products is facilitated by a number of factors related to the use of oxygen in place of hydrogen peroxide. The isolation of the final products is simplified both because the final reaction volume is reduced and because the amount of water generated as a side product of the reaction is decreased. Further, since the peroxidant is substantially consumed during the course of the reaction, the need to decompose residual excess peroxidant as part of the workup and isolation procedures is avoided.

DETAILED DESCRIPTION OF THE INVENTION

The present invention provides a method for the preparation of a carboxylic acid from an olefin or a vicinal dihydroxy compound. The method includes contacting the olefinic or vicinal dihydroxy compound with oxygen in the presence of a protic organic solvent, an inorganic oxide catalyst and a peroxidant. As shown in equation (C), the oxidation of an olefin to carboxylic acids via the present method only requires that 1.0 equivalent of a peroxidant (e.g., hydrogen peroxide or a peralkanoic acid such as peracetic acid) be used. Although the present invention is not limited by this explanation, it is believed that in the presence of the peroxidant, the olefin is oxidized to an epoxide compound. The epoxide is believed to be hydrolyzed under the reaction conditions to a vicinal dihydroxy compound. As shown in equation (D), the present method for oxidatively cleaving a vicinal dihydroxy compound does not require hydrogen peroxide as a stoichiometric reagent to carry out the oxidation. It is believed that a small amount of a peroxidant, however, must be present in order for the oxidation of the vicinal dihydroxy compound to proceed. While not a limitation on the invention, it is believed that the peroxidant reacts with the inorganic oxide catalyst to form an activated catalyst species. This may occur during the oxidation of an olefin with hydrogen peroxide in the presence of the inorganic oxide catalyst or through the direct reaction of a small amount (typically at least about 1.0 equivalents based on the amount of inorganic oxide catalyst present) of the peroxidant with the inorganic oxide catalyst during the initial phase of the oxidation of a vicinal dihydroxy compound with oxygen.

(C) RCH=CHR'+H$_2$O$_2$→RCHOH—CHOHR'

(D) RCHOH—CHOHR'+1.5 O$_2$→RCO$_2$H+R'CO$_2$H+H$_2$O

The inorganic oxide catalyst employed in the present method typically includes an inorganic oxide compound such as an oxide of tungsten, molybdenum, niobium, vanadium, tantalum, titanium, or yttrium. In addition to simple oxides (e.g., WO$_3$), inorganic oxyacids and related heteropoly acids are included among such inorganic oxides. For example, tungstic acid, molybdic acid and related heteropoly acids are useful as catalysts in the present method. As used herein such "heteropoly acids" refer to a polyacid which includes at least a second heteroatom in addition to the primary metal in the oxide (e.g., an oxyacid which includes a tungsten or molybdenum atom in addition to at least one other heteroatom. Phosphorous, arsenic, silicon, titanium, iron, boron, nickel, uranium, and the like are examples of heteroatoms which may be used in the formation of heteropoly acids. Heteropoly acids containing phosphorous or silicon as the heteroatom are typically preferred because of the ease of preparation or availability of starting materials. Commonly known heteropoly acids which may be employed in the present invention include 12-tungstophosphoric acid (H$_3$PW$_{12}$O$_{40}$), 12-tungstosilicic acid (H$_3$SiW$_{12}$O$_{40}$) and 12-molybdophosphoric acid (H$_3$PMo$_{12}$O$_{40}$).

While the present method is commonly carried out using a catalyst which includes tungstic acid or molybdic acid, related oxides such as WO$_2$, W$_2$O$_5$, WO$_3$, or MoO$_3$ may also be employed. In addition, tungsten or molybdenum compounds which are capable of being transformed into a tungstate or molybdate ion in the reaction medium (e.g., chlorides or sulfides) may also be used in the present invention.

The inorganic oxide catalyst employed in the present invention may include oxides of niobium, vanadium, tantalum, titanium, or yttrium. As with tungsten and molybdenum oxides, corresponding metal compounds which are capable of being transformed into an appropriate metal oxide or metal ion in the reaction medium (e.g., chlorides or sulfides such as MoS$_3$ or VCl$_3$) may also be used in the present invention.

In a preferred embodiment of the invention the inorganic oxide catalyst includes a tungsten oxide and more preferably, includes tungstic acid or WO$_3$. In addition, it has been found that mixed catalyst systems, e.g., mixed catalysts which include a tungsten oxide, may be employed in the present method. For example, mixtures of tungstic acid and another inorganic transition compound such as an inorganic molybdenum compound, an inorganic niobium compound, an inorganic iron compound, or an inorganic titanium compound may be employed. Suitable mixed catalysts systems which may be used in the present oxidative cleavage reaction includes mixtures of tungstic acid with molybdic acid, titanium dioxide (TiO$_2$), titanium oxalate (Ti$_2$(C$_2$O$_4$)$_3$), niobium oxide (Nb$_2$O$_5$), or ferric oxide (Fe$_2$O$_3$). Although less preferred, mixtures of tungstic acid with vanadium oxide (V$_2$O$_5$) or cobalt (II) chloride may also be employed as a mixed catalyst system in the present invention.

In another preferred embodiment of the invention, the inorganic oxide catalyst employed in the present method includes tungstic acid, tungsten trioxide, molybdic acid or niobium pentoxide. More preferably, the inorganic oxide catalyst includes tungstic acid.

The peroxidant includes a peroxide ("—O—O—") bond. As indicated above, the peroxidant is believed to serve at least two functions in the present method. When the present method is used to oxidatively cleave an olefin, the peroxidant acts as the major oxidant in the conversion of the olefin into the corresponding vicinal dihydroxy compound (see e.g., equation (C) above). While not a limitation of the present invention, the presence of the peroxidant is also believed to be required in order to convert the inorganic oxide catalyst into an activated form. Examples of suitable peroxidants include hydrogen peroxide (H$_2$O$_2$) and peralkanoic acids such as peracetic acid.

The present method allows the preparation of a carboxylic acid from either an olefin or a vicinal dihydroxy compound. The method is especially suitable for oxidatively cleaving an unsaturated acid or the corresponding vicinal dihydroxy compound to yield a carboxylic acid. Examples of unsaturated acids which are suitable for use in the practice of the present invention, include oleic acid, linoleic acid, linolenic acid, eleostearic acid, licanic acid, parinaric acid, ricinoleic acid, palmitoleic acid, petroselinic acid, vaccenic acid, erucic acid and mixtures thereof. Likewise, the ethylenic group of esters of these acids, especially the methyl, ethyl and propyl esters, or the corresponding amides may be oxidatively cleaved to acids by the process of this invention. Likewise the natural fats and oils (which are esters of glycerol) are commonly saponified to give mixtures of saturated and unsaturated acids. Such mixtures contain, for example, lauric acid, palmitic acid, and stearic acid together with some or all of the unsaturated acids hereinbefore noted. Such commercially available acid mixtures can be oxidized to mixtures of acids by the present process and are suitable for use herein. The saturated acids present in such mixtures are not involved in the reaction since, by virtue of their lack of an olefinic linkage, they are not oxidized; the saturated acids can, of course, be removed by standard purification procedures.

In addition, any of the common sources of unsaturated acid mixtures can be used to provide acids which can be oxidized in accordance with the present invention. Palm oil, coconut oil, babassu oil, lard, tallow, castor oil, olive oil, peanut oil, corn oil, sesame oil, cottonseed oil, soybean oil, sunflower oil, hemp oil, linseed oil, tung oil, oiticica oil, whale oil, Neat's-foot oil and the like, can all be saponified and yield unsaturated acids which can then be oxidized in the present process.

Unsaturated hydrocarbons may also be oxidatively cleaved using the present method. For example, unsaturated aliphatic hydrocarbons such a cis-2-octene and 1-hexadecene may be oxidized using the present method to yield hexanoic acid and pentadecanoic acid respectively.

The present method includes contacting an olefinic compound or a vicinal dihydroxy compound with oxygen in the presence of a protic organic solvent. The protic organic solvent includes a saturated hydrocarbon alcohol or a saturated hydrocarbon acid. Typically the solvent includes a saturated tertiary alcohol such as t-butanol, t-amyl alcohol, 1-methylcyclopentanol or 1-methylcyclohexanol. The solvent may include a saturated hydrocarbon acid such as acetic acid. The use of hydrocarbon acids in the present method is less preferred, as such acids may have a tendency to esterify vicinal dihydroxy compounds, thereby blocking reaction with the inorganic oxide catalyst and lowering the yield of the reaction. When a number of factors including yield, cost, ease of handling and ease of removal are taken into consideration, t-butanol is among the preferred solvents for use with the present invention.

The reaction time necessary to carry out the present reaction will vary depending on the concentration of substrate, catalyst, dissolved oxygen and/or peroxidant, the pressure under which the reaction is run, the reaction temperature, and the like. Typical reaction times range from about 1 to about 48 hours. By altering the reaction conditions, shorter or longer reaction times may be achieved.

The present method typically employs the inorganic oxide catalyst in an amount of about 0.001 to about 10 equivalent (gram atom of metal in the metal oxide) per mole of substrate (olefin or vicinal dihydroxy compound). When the present method is carried out in a batch mode, about 0.05 to about 1.0 equivalents of the inorganic oxide catalyst per mole of substrate are preferably employed.

In order to avoid the problems associated with the use of larger amounts of the peroxidant, the present method preferably employs the minimal amount of peroxidant required. For the oxidation of an olefin to a carboxylic acid, the present method is carried out in the presence of at least about 1.0 equivalent of peroxidant (e.g., $H_2O_2$) per mole of substrate. Although the use of larger amounts of peroxidant is not preferred, the advantages of the present method may be realized to some extent even when up to about 2.0 equivalents of peroxidant per mole of substrate are employed in the oxidation of an olefin. Preferably, the present method of oxidatively cleaving an olefin is conducted using from about 1.0 to about 1.5 equivalents and, more preferably, from about 1.0 to about 1.1 equivalents of peroxidant per mole of olefinic compound.

When the present method is utilized to cleave a vicinal dihydroxy compound to yield a carboxylic acid, the reaction is carried out in the presence of a sufficient amount of the peroxidant to activate the inorganic oxide catalyst. Typically, the amount of peroxidant employed is a substoichiometric amount with respect to what would be required to carry out the oxidative cleavage of the dihydroxy compound to a carboxylic acid. Preferably, the ratio of the molar ratio of the peroxidant to the dihydroxy compound is no more than about 1:1. in general, at least about 0.01 equivalent and no more than about 20 equivalents of peroxidant per mole of the inorganic metal oxide (per gram atom of metal in the metal oxide) is employed in the oxidative cleavage of a vicinal dihydroxy compound. Preferably, the oxidative cleavage of the dihydroxy compound is carried out in the presence of about 0.1 to about 10 equivalents of peroxidant per mole of inorganic metal oxide. More preferably, the oxidative cleavage is run in the presence of about one equivalent (i.e., from about 0.5 to about 2 equivalents) of peroxidant per mole of inorganic metal oxide.

When run at about ambient pressure, the reaction is usually carried out at a temperature of about 20° C. to about 130° C. When the reaction is conducted at an elevated pressure in order to maintain a sufficient concentration of dissolved oxygen, a reaction temperature of up to about 300° C or higher may be employed. Generally, it is preferred to conduct the reaction at a temperature of about 50° C. to about 150° C. to increase the reaction rate while preventing or inhibiting the decomposition of the peroxidant.

The present method is typically carried out with the oxygen being introduced to the reaction mixture via a gas stream which is bubbled through the mixture. However, where the present method is carried out under an elevated pressure of an oxygen containing gas and/or the reaction mixture is subjected to sufficiently vigorous stirring, the oxygen may be introduced to the reaction mixture simply by maintaining an upper oxygen containing gas phase in contact with the reaction mixture.

While for practical reasons the reaction is typically run at atmospheric pressure, the rate of the reaction may also be increased by carrying out the oxidative cleavage at an elevated pressure. This increases the concentration of dissolved oxygen and also permits the reaction to be run at a higher temperature. When the reaction is carried out at an ambient pressure, increasing the temperature results in a decrease in the dissolved oxygen concentration. Because of this, an increase in temperature may actually result in a slower rate of reaction. The use of elevated pressure allows the present method to be run at a higher temperature without lowering the concentration of dissolved oxygen. The present method is preferably carried out under a pressure of slightly below ambient pressure (slightly less than one atmosphere) to about 100 atmospheres.

The reaction between the olefin or dihydroxy compound and oxygen is facilitated by vigorous stirring of the reaction mixture. By the term "vigorous stirring" is intended stirring that is sufficient to create a continuous mixing throughout the solution and to maintain the inorganic oxide catalyst relatively evenly distributed throughout the reaction mixture. The use of vigorous stirring is particular advantageous where the inorganic oxide catalyst is sparing soluble or substantially insoluble in the reaction mixture. The term "vigorous stirring" also implies stirring that is sufficient to maintain efficient contact between the reactants and to facilitate mass transport.

After completion of the reaction, the carboxylic acid produced can be separated from the reaction product by a variety of conventional methods. In some instances (e.g., where the catalyst is soluble in the reaction mixture) it may be advantageous to gradually cool the reaction mixture to permit the carboxylic acid to crystallize. The catalyst, however, is typically substantially insoluble in the reaction mixture, thus allowing removal/recovery of the catalyst by filtration. The product carboxylic acid may then be isolated from the mother liquor by standard methods such as removal of the solvent via distillation, extractive techniques, and/or chromatography.

The invention will be further described by reference to the following detailed examples.

EXAMPLE 1

$H_2WO_4$ Catalyzed Aerobic Oxidative Cleavage of Erucic Acid

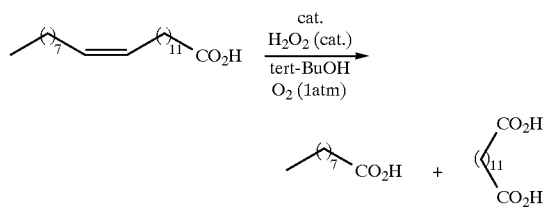

In the presence of oxygen, erucic acid (0.338 g, 1.0 mmol; recrystallized from 95% ethanol), t-butanol (2 ml; freshly distilled), and $H_2O_2$ (30% aqueous solution, amount shown in Table I) and tungstic acid (24.9 mg, 0.1 mmol) was added to a 10-ml three-necked flask equipped with refluxing condenser. A stream of oxygen gas was bubbled through the mixture as the mixture was heated to reflux. The reaction was monitored with either TLC (ethyl acetate/hexane) or GC (HP-INNOWAX column; crosslinked polyethylene glycol). After the reaction was completed, the yellow catalyst was filtered off and washed with hot methanol (1 ml) at once. The catalyst was recovered (about 100%). Most of the solvent in the mother liquors was removed under reduced pressure. The results of a number of experiments following this procedure and using a varying amount of $H_2O_2$ are reported in Table I herein. The yield of the reaction (based on brassylic acid) was determined by one of the following methods.

Method A: The residue from the mother liquors was extracted with ethyl acetate (5×10 ml) and dried (anhydrous $MgSO_4$). The drying reagent was filtered off and the solvent was removed under reduced pressure. Dry methanol (5 ml) and 1 drop of concentrated sulfuric acid were then added to the residue. The resulting solution was refluxed for 2 hours. The methanol was removed and 0.5 ml of water was added to the mixture. The mixture was extracted with ethyl acetate (3×5 ml) and the ethyl acetate extracts were combined and dried (anhydrous $MgSO_4$) The solvent was then removed yielding dimethyl brassylate and methyl nonanoate. The identities of the products were confirmed by spectroscopic analysis, including nuclear magnetic resonance, infrared spectroscopy and mass spectroscopy. The yield of dimethyl brassylate is reported in Table I.

Method B: The residue from the mother liquors was placed in a freezer (circa –5° C.) for about 5 hours. After a white solid appeared, hexane (5 ml) was added. The resulting solid, brassylic acid, was isolated by filtration. The brassylic acid was purified by recrystallization in methanol to yield a white solid (mp: 110–114° C.).

TABLE I

Effect of $H_2O_2$

| Entry | Catalyst | $H_2O_2$ (eq) | Reaction Time (h) | Yield (%) |
| --- | --- | --- | --- | --- |
| 1 | $H_2WO_4$ | 4 | 18 | 84[a] |
| 2 | $H_2WO_4$ | 2 | 24 | 88[a] |
| 3 | $H_2WO_4$ | 1 | 30 | 81[a] |
| 4 | $H_2WO_4$ | 1 | 24 | 91[b] |
| 5 | $H_2WO_4$ | 0.5 | 24 | 6 |
| 6 | $H_2WO_4$ | — | 50 | 0 |

[a]Isolated yield of brassylic acid; [b]GC yield of dimethyl brassylate.

EXAMPLE 2

Large Scale $H_2WO_4$ Catalyzed Aerobic Oxidative Cleavage of Erucic Acid

To a 1000-ml three-necked flask equipped with refluxing condenser and mechanic stirrer, erucic acid (101.4 g, 0.300 mol; recrystallized with 95% ethanol), tert-butanol (600 ml; freshly distilled), $H_2O_2$ (20.4 ml 50% aqueous solution, 0.3 mol) and tungstic acid (7.47 g, 0.03 mol). The mixture was refluxed for 70 hours while a stream of oxygen gas was bubbled through the solution. The reaction was monitored with TLC (ethyl acetate/hexane). After the reaction was completed, the yellow catalyst was filtered off and washed with hot methanol (2×20 ml) at once. The catalyst was recovered (about 100%). Most of the solvent in the mother liquor was removed under reduced pressure. The residue was then held at about –5° C. for several hours. Once a white solid appeared, hexane (100 ml) was added. The product brassylic acid was obtained by filtration (63.2 g, 76%). The brassylic acid was purified by recrystallization in methanol.

(mp: 110°–114° C.) The stoichiometry of the reaction dictates that the oxidative cleavage of a 1,2-disubstituted olefinic double bond results in the formation of equal amounts of pelargonic acid and brassylic acid. Of the two acids formed, the generation of brassylic acid was monitored simply due to the relative ease of the analysis.

EXAMPLE 3

$H_2WO_4$ Catalyzed Aerobic Oxidative Cleavage of Erucic Acid—Effect of Replacement of $H_2O_2$ The effect of replacing the $H_2O_2$ with a variety of additives on the yield of the oxidative cleavage reaction was studied. With the exception of the replacement of the $H_2O_2$ with the indicated additive, the reaction procedure and stoichiometry were as described in Example 1. The results shown in Table II below indicate a peralkanoic acid (peracetic acid) was the only additive other than $H_2O_2$ which resulted in the oxidative cleavage of the double bond of erucic acid to yield two carboxylic acids. The yields reported are based on brassylic acid.

TABLE II

Effect of Additives

| Entry | Catalyst | Additives (eq) | Reaction Time (h) | Yield (%) |
| --- | --- | --- | --- | --- |
| 1 | $H_2WO_4$ | $CuCl_2.6H_2O$ (0.1) | 40 | 0 |
| 2 | $H_2WO_4$ | $CoCl_2.6H_2O$ (0.1) | 40 | 0 |
| 3 | $H_2WO_4$ | i-PrCHO (0.1) | 40 | 0 |
| 4 | $H_2WO_4$ | $HOCH_2CH_2OH$ (0.1) | 30 | 0 |
| 5 | $H_2WO_4$ | pyromatellatic acid (0.1) | 30 | 0 |
| 6 | $H_2WO_4$ | $H_2O_2$(1) | 24 | 91 |
| 7 | $H_2WO_4$ | m-CPBA (1) | 24 | 0 |
| 8 | $H_2WO_4$ | $K_2S_2O_8$ (1) | 24 | 0 |
| 9 | $H_2WO_4$ | t-BuOOH (1.0) | 24 | 0 |
| 10a | $H_2WO_4$ | AcOOH | 12 | 4 |
| 10b | | | 24 | 30 |

EXAMPLE 4

Catalyzed Aerobic Oxidative Cleavage of Erucic Acid—Effectiveness of Other Catalysts The ability of other metal oxide catalysts to catalyze the oxidative cleavage of erucic acid in the presence of oxygen and 1.0 equivalent of $H_2O_2$, was examined using the procedure described in Example 1 herein. The amount and type of catalyst employed is shown in Table III. The yields reported are the yield of brassylic acid (which reflects the amount of pelargonic acid formed) as determined by GC. The results demonstrate that erucic acid can be oxidatively cleaved using oxygen in the presence of 1.0 equivalent (based on erucic acid) of $H_2O_2$ and a variety of transition metal oxide catalysts.

TABLE III

Effect of Catalysts

| Entry | Catalyst (eq) | Reaction Time (h) | Yield (%) |
| --- | --- | --- | --- |
| 1 | $H_2WO_4$ (0.1) | 24 | 91 |
| 2 | $H_2WO_4$ (0.3) | 24 | 15 |
| 3a | $H_2WO_4$ (0.05) | 24 | 3 |
| 3b | | 40 | >90 |

TABLE III-continued

Effect of Catalysts

| Entry | Catalyst (eq) | Reaction Time (h) | Yield (%) |
|---|---|---|---|
| 4 | $H_3PO_4.(WO_3)_{12}.x\ H_2O$ (0.1) | 24 | 20 |
| 5 | $WO_3$ (0.1) | 24 | 70 |
| 6 | $WO_3$ (0.1) + $H_3^+O$ (PH = 0.4) | 24 | 70 |
| 7 | $H_2SiO_4.(WO_3)_{12}.x\ H_2O$ (0.1) | 24 | 5 |
| 8 | $H_2MoO_4$ (0.1) | 24 | 32 |
| 9 | $P_2O_5\ (MoO_3)_{20}.x\ H_2O$ (0.1) | 24 | 15 |
| 10a | $Y_2O_3$ (0.1) | 24 | 3 |
| 10b | | 48 | 14 |
| 11 | $Gd_2O_3$ (0.1) | 24 | 0 |
| 12 | $V_2O_5$ (0.1) | 24 | 10.2 |
| 13 | $La_2O_3$ (0.1) | 24 | 0 |
| 14a | $Ta_2O_5$ (0.1) | 24 | 2.3 |
| 14b | | 48 | 15 |
| 15 | $Nb_2O_5$ (0.1) | 24 | 24 |
| 16 | $Nb_2O_5$ (0.1)/$H_3^+O$ (PH = 4) | 24 | 10 |
| 17 | $VCl_3$ (0.1) | 24 | 3 |
| 18 | $TiO_2$ (0.1) | 24 | 4.4 |
| 19 | $CoWO_7$ (0.1) | 24 | 0 |

EXAMPLE 5

Catalyzed Aerobic Oxidative Cleavage of Erucic Acid—Effectiveness of Mixed Catalysts The ability of a number of mixed metal oxide catalysts to catalyze the oxidative cleavage of erucic acid in the presence of oxygen and 1.0 equivalent of $H_2O_2$ was examined using the procedure described in Example 1 herein. The amount and type of catalyst employed is shown in Table IV. In each case, 10 mol% $H_2WO_4$ (based on erucic acid) was used together with the indicated amount of the other inorganic catalyst. The molar ratio of the two catalysts are shown in parentheses. The yields reported are the yield of brassylic acid as determined by GC. The results demonstrate that erucic acid can be oxidatively cleaved using oxygen in the presence of 1.0 equivalent (based on erucic acid) of $H_2O_2$ and a variety of mixed transition metal oxide catalysts. Although none of the yields shown with a mixed catalyst system are higher than that reported with $H_2WO_4$ alone, the rate of the reaction was considerably faster with the $H_2WO_4$/$Nb_2O_5$ mixed catalyst (reaction completed after about 16 hr.; 87% yield) than with $H_2WO_4$ alone (91% yield after 24 hr.).

TABLE IV

Effect of Mixed Catalysts.

| Entry | Catalyst | Reaction Time (h) | Yield (%) |
|---|---|---|---|
| 1 | $H_2WO_4/V_2O_5$ (10:1) | 24 | 6 |
| 2 | $H_2WO_4/H_2MoO4$ (10:1) | 24 | 67 |
| 3 | $H_2WO_4/COCl_2.6\ H_2O$ (10:1) | 24 | 18 |
| 4 | $H_2WO_4/Nb_2O_5$ (10:1) | 16 | 87 |
| 5 | $H_2WO_4/Fe_2O_3$ (10:1) | 24 | 80 |
| 6 | $H_2WO_4/Ti_2(C_2O_4)_3$ (10:1) | 24 | 76 |
| 7 | $H_2WO_4/Nb_2O_5$ (1:1) | 24 | 74 |
| 8 | $H_2WO_4/TiO_2$ (10:1) | 24 | 64 |
| 9 | $H_2WO_4/$ - (10:-) | 24 | 91 |
| 10 | - /$H_2MoO_4$ (- :10) | 24 | 32 |

EXAMPLE 6

Catalyzed Aerobic Oxidative Cleavage of Erucic Acid—Effective of Solvent Variation The effect of various solvents on the $H_2WO_4$ catalyzed oxidative cleavage of erucic acid was examined using the procedure described in Example 1 herein. The results obtained are shown in Table V. The yields reported are of brassylic acid as determined by GC. The results demonstrate that erucic acid can be oxidatively cleaved by oxygen in the presence of an inorganic oxide catalyst, a peroxidant and a protic organic solvent such as t-butanol or acetic acid.

TABLE V

Effect of Solvents

| Entry | Solvent | Time (h) | Yield (%) |
|---|---|---|---|
| 1 | — | 24 | 0 |
| 2 | HOAc | 24 | 12 |
| 3 | $H_2O$ | 24 | 0 |
| 4 | t-BuOH | 24 | 91 |
| 5 | DMF(80°) | 24 | 0 |
| 6 | i-PrOH | 48 | Diol Only |
| 7 | Cyclohexanol | 48 | 6 |

EXAMPLE 7

Catalyzed Aerobic Oxidative Cleavage of Olefinic Compounds

The $H_2WO_4$ catalyzed oxidative cleavage of a variety of olefinic compounds in t-butanol with oxygen was examined using the procedure described in Example 1 herein. The isolated yields obtained for the corresponding carboxylic acid products are shown in Table VI. The product of the oxidative cleavage of oleic acid (entry 5) was isolated as the corresponding azaleic acid.

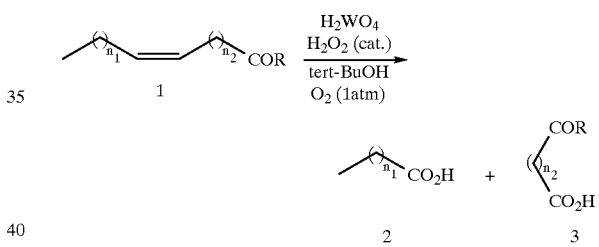

TABLE VI

Tungstic Acid Catalyzed Oxidative Cleavage of Olefinic Compounds in the Presence of $O_2$,[a]

| | Substrate | | | Reaction | | Isolated |
|---|---|---|---|---|---|---|
| Entry | $n_1$ | $n_2$ | R | time (h) | Product | yield (%) |
| 1 | 7 | 11 | CH(1a) | 30 | 3a[b] | 87 |
| 2 | 7 | 11 | OMe(1b) | 24 | 3b[c] | 79 |
| 3 | 7 | 11 | OEt(1c) | 26 | 3c[c] | 72 |
| 4 | 7 | 11 | $NH_2$(1d) | 26 | 3d[d] | 94 |
| 5 | 7 | 7 | CH(1e) | 26 | 3e[c] | 92 |
| 6 | cyclohexene | | (1g) | 50 | | 0 |
| 7 | cyclododecene | | | 50 | | 0 |
| 8 | cis-2-octene | | | 24 | | 28 |
| 9 | 1-hexadecene | | | 24 | | 24 |

[a]Reaction conditions: The mixture of 1 (1 mmol), $H_2WO_4$(25 mg, 0.1 mmol), $H_2O_2$ (50%) (0.08 ml, 0.1 mmol) and tert-BuOH (4 ml) was refluxed under $O_2$. [b]10 mmol scale (3.38 g) of 1a; C: The product was isolated as ester and confirmed by GC analysis; [d]3d was isolated: mp 112–115° C.

EXAMPLE 8

Isolation of a Vicinal Dihydroxy Intermediate

To a 100-ml three-necked flask equipped with refluxing condenser, was added erucic acid (recrystallized with 95% ethanol; 3.38 g, 10 mmol), t-butanol (20 ml; freshly distilled), $H_2O_2$ (0.68 ml 50% solution, 10 mmol) and tungstic acid (249 mg, 1 mmol). The mixture was then refluxed for 3 hours. Monitoring by GC showed that most of the starting material had reacted at this point. The reaction was stopped and the yellow catalyst was filtered off and washed with hot methanol (1 ml) at once. The catalyst was recovered (about 100%). The solvent in the mother liquor was removed. The residue was then subjected to column chromatography (eluent: ethyl acetate). A white solid was obtained and confirmed to be 12,13-dihydroxydocosenoic acid by proton and carbon NMR.

EXAMPLE 9

Oxidative Cleavage of Dihydroxy Acids 12,13-Dihydroxydocosenoic acid was oxidatively cleaved with oxygen using the procedure described in Example 1 herein. The dihydroxy acids were heated in the presence of $H_2WO_4$ (10 mol% based on dihydroxy compound) and optionally $H_2O_2$ (amount based on dihydroxy compound) in the indicated solvent while oxygen was bubbled through the reaction mixture. Unless otherwise indicated, the reactions were carried out at the reflux temperature of the solvent. The results shown in Table VII below indicate that a vicinal dihydroxy compound can be oxidatively cleaved using oxygen in the presence of a tungsten oxide catalyst and amount of a peroxidant (e.g., $H_2O_2$) which is sufficient to activate the inorganic oxide catalyst. In addition to the results shown in Table VII, oxygen was bubbled through a solution of cis-1,2-cyclohexanediol in t-butanol containing $H_2WO_4$ (0.1 eq. based on diol) and $H_2O_2$ (0.5 eq. based on diol). After heating the reaction mixture to reflux for 12 hours, a 77% yield (based on starting diol) of adipic acid was obtained.

TABLE VII

Tungstic Acid Catalyzed Oxidative Cleavage of 12,13-Dihydroxydocosenoic Acid in the Presence of $O_2$

| Entry | Solvent | $H_2O_2$(eq) | Time (h) | Yield (%) |
|---|---|---|---|---|
| 1a | t-Butanol | — | 12 | 0 |
| 1b | | — | 24 | 0 |
| 2a | t-Butanol | 1.0 | 12 | 68 |
| 2b | | | 24 | >90 |
| 3 | t-Butanol | 0.5 | 15 | 79 |
| 4 | DMF (80°) | 1.0 | 24 | 0 |

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

What is claimed is:

1. A method for preparing a carboxylic acid comprising:
   contacting an olefinic compound with oxygen in the presence of a protic organic solvent, an inorganic oxide catalyst and a peroxidant;
   the inorganic oxide catalyst including an oxide of tungsten and an oxide of niobium;
   the peroxidant including hydrogen peroxide or a peralkanoic acid.

2. The method of claim 1 wherein the molar ratio of the peroxidant to the olefinic compound is from about 1:1 to about 2:1.

3. The method of claim 2 wherein the tungsten oxide comprises tungstic acid or $WO_3$.

4. The method of claim 2 wherein the tungsten oxide comprises a heteropoly acid of tungstic acid.

5. The method of claim 2 wherein the inorganic oxide catalyst further comprises an inorganic molybdenum compound, an inorganic niobium compound, an inorganic iron compound, or an inorganic titanium compound.

6. The method of claim 1 wherein the protic organic solvent comprises a saturated hydrocarbon alcohol or a saturated hydrocarbon acid.

7. The method of claim 6 wherein the saturated hydrocarbon alcohol comprises a tertiary alcohol.

8. The method of claim 7 wherein the tertiary alcohol includes t-butanol.

9. The method of claim 1 wherein the olefinic compound comprises an unsaturated fatty acid, an unsaturated fatty acid ester or an unsaturated fatty acid amide.

10. The method of claim 1 comprising contacting the olefinic compound with oxygen under a pressure of about 1.0 to about 100 atmospheres at a temperature of about 20° C. to about 300° C.

11. The method of claim 1 wherein the protic organic solvent includes t-butanol; the inorganic oxide catalyst includes tungstic acid and $Nb_2O_5$; and the peroxidant includes hydrogen peroxide.

12. A method for preparing a carboxylic acid comprising:
   contacting a vicinal dihydroxy compound with oxygen in the presence of an inorganic oxide catalyst and a peroxidant;
   wherein the inorganic oxide catalyst includes an oxide of tungsten and an oxide of niobium; and
   and the peroxidant includes hydrogen peroxide or a peralkanoic acid.

13. The method of claim 12 wherein the molar ratio of the peroxidant to the vicinal dihydroxy compound is no more than about 1:1.

14. The method of claim 12 wherein the molar ratio of the peroxidant to the inorganic oxide catalyst is from about 0.01 to about 20:1.

15. The method of claim 12 comprising contacting the vicinal dihydroxy compound with oxygen under a pressure of about 1.0 to about 100 atmospheres at a temperature of about 20° C. to about 300° C.

16. The method of claim 12 wherein the peroxidant includes hydrogen peroxide.

* * * * *